(12) United States Patent
Silver

(10) Patent No.: US 8,430,842 B2
(45) Date of Patent: *Apr. 30, 2013

(54) MANUAL BREASTPUMP WITH STIMULATION FEATURE

(75) Inventor: Brian H. Silver, Cary, IL (US)

(73) Assignee: Medela Holding AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/711,783

(22) Filed: Feb. 24, 2010

(65) Prior Publication Data

US 2010/0217183 A1 Aug. 26, 2010

Related U.S. Application Data

(62) Division of application No. 10/424,887, filed on Apr. 28, 2003, now Pat. No. 7,727,182.

(60) Provisional application No. 60/405,559, filed on Aug. 23, 2002.

(51) Int. Cl.
*A61M 1/06* (2006.01)

(52) U.S. Cl.
USPC .......................................................... 604/74

(58) Field of Classification Search ............... 604/72–75
See application file for complete search history.

(56) References Cited

U.S. PATENT DOCUMENTS

| 37,677 | A | | 2/1863 | Colrin |
|---|---|---|---|---|
| 4,263,912 | A | * | 4/1981 | Adams ............................ 604/75 |
| 4,583,970 | A | * | 4/1986 | Kirchner ......................... 604/74 |
| 4,813,932 | A | | 3/1989 | Hobbs |
| 4,857,051 | A | | 8/1989 | Larsson |
| 4,929,229 | A | | 5/1990 | Larsson |
| 5,843,029 | A | | 12/1998 | Bachman et al. |
| 6,110,140 | A | | 8/2000 | Silver |
| 6,547,756 | B1 | | 4/2003 | Greter et al. |
| 6,689,073 | B2 | | 2/2004 | Quay |
| 6,749,582 | B2 | | 6/2004 | Britto et al. |

FOREIGN PATENT DOCUMENTS

| WO | 0147577 A2 | 7/2001 |
|---|---|---|
| WO | 0147577 A3 | 7/2001 |
| WO | 03013628 A1 | 2/2003 |
| WO | 2004000390 A1 | 12/2003 |

* cited by examiner

*Primary Examiner* — Matthew F DeSanto
(74) *Attorney, Agent, or Firm* — McDonnell Boehnen Hulbert & Berghoff LLP

(57) ABSTRACT

A manual breastpump has a pump mechanism for use in one mode of operation to produce an ejection (letdown) reflex in a nursing mother and in a separate mode of operation for the general expression of breastmilk. The breastpump further provides a pump mechanism having an expansible chamber device carried by the handle, which is operated by moving the handle relative to a handle mount. A double-pivot for the handle yields letdown mode as well as the general pumping mode.

9 Claims, 5 Drawing Sheets

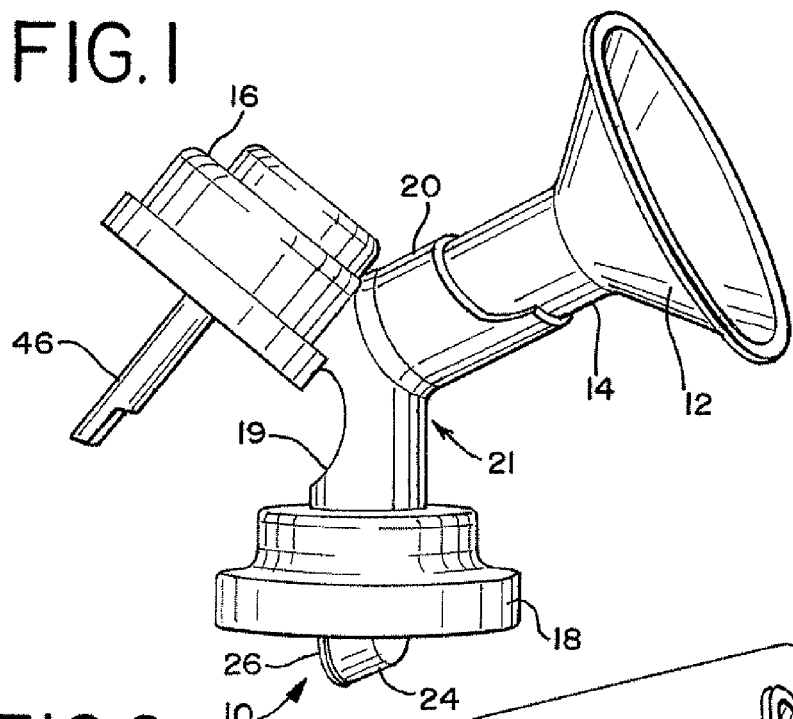
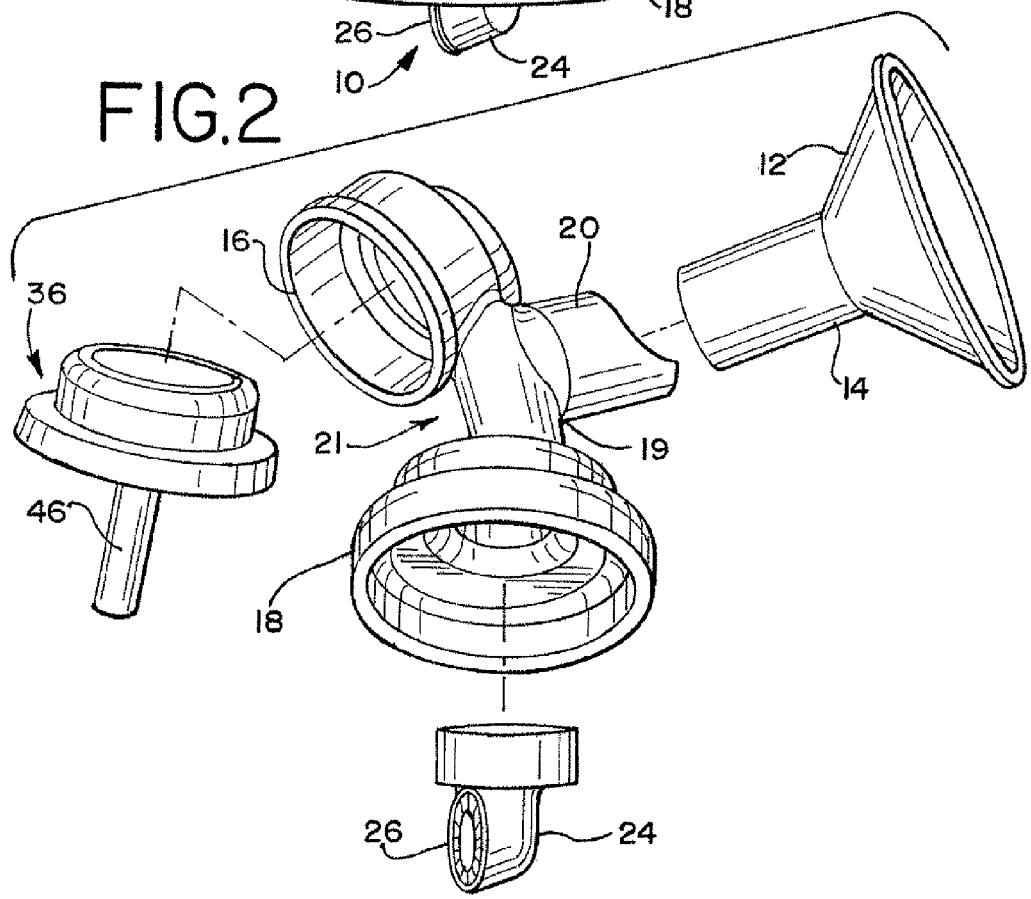

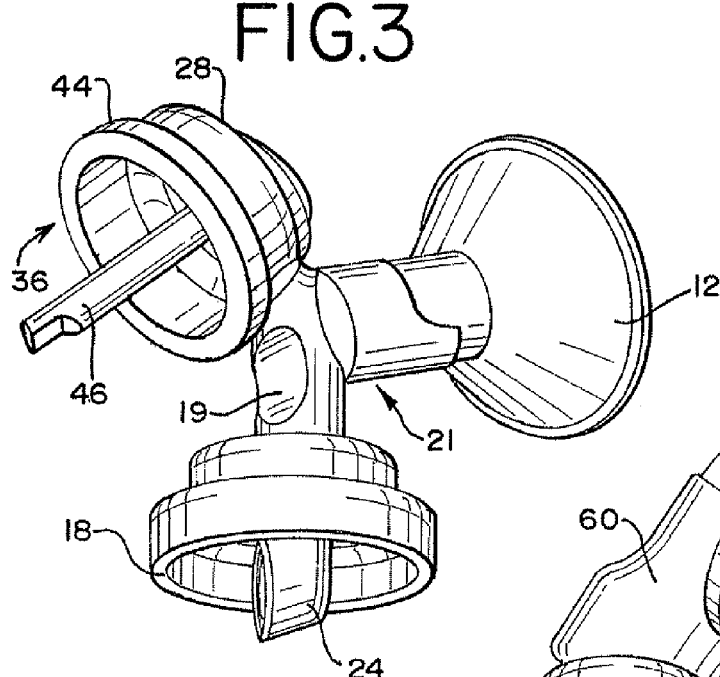
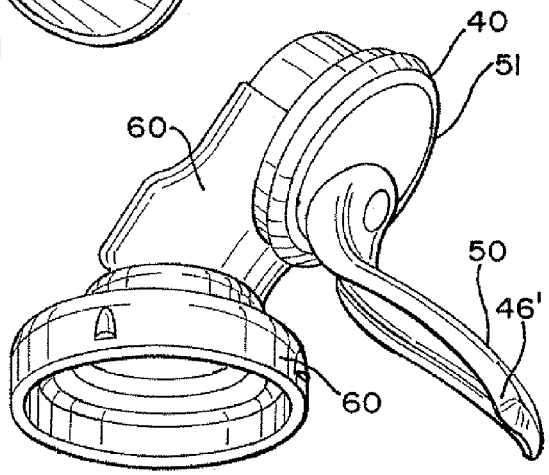
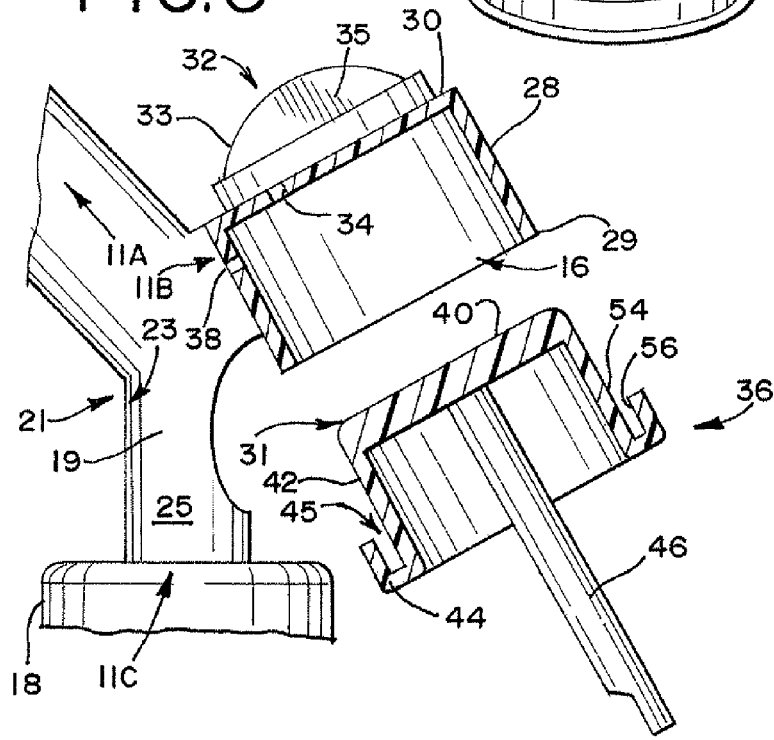

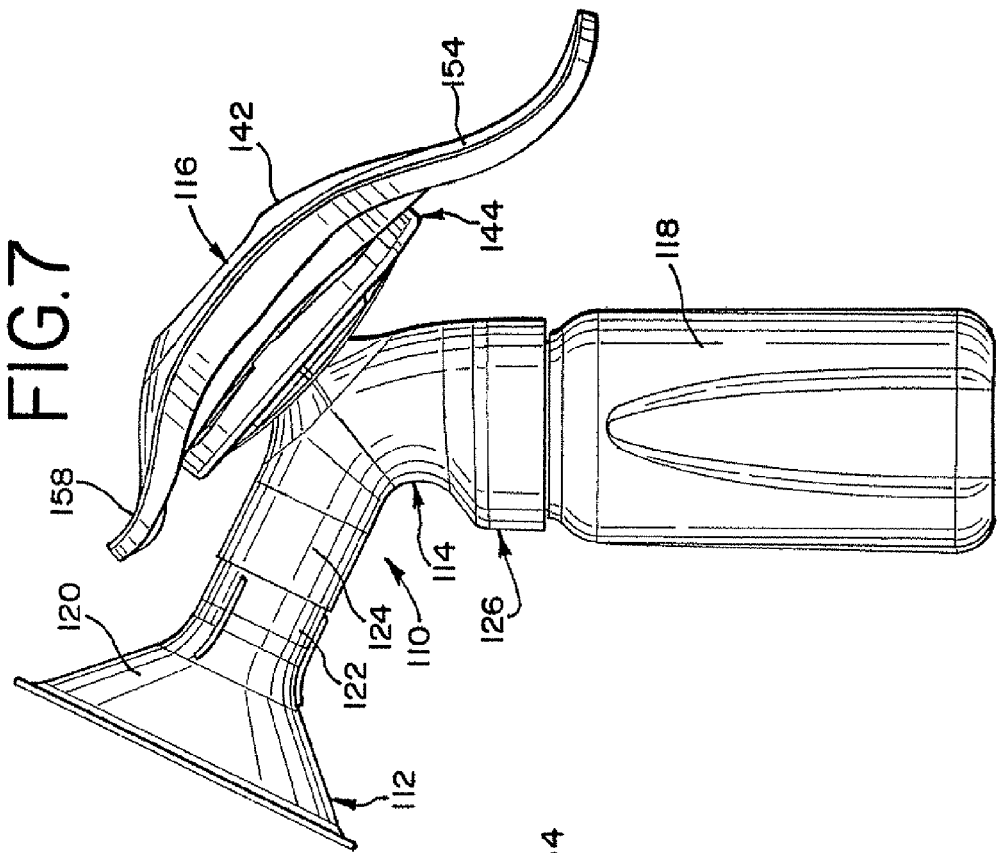
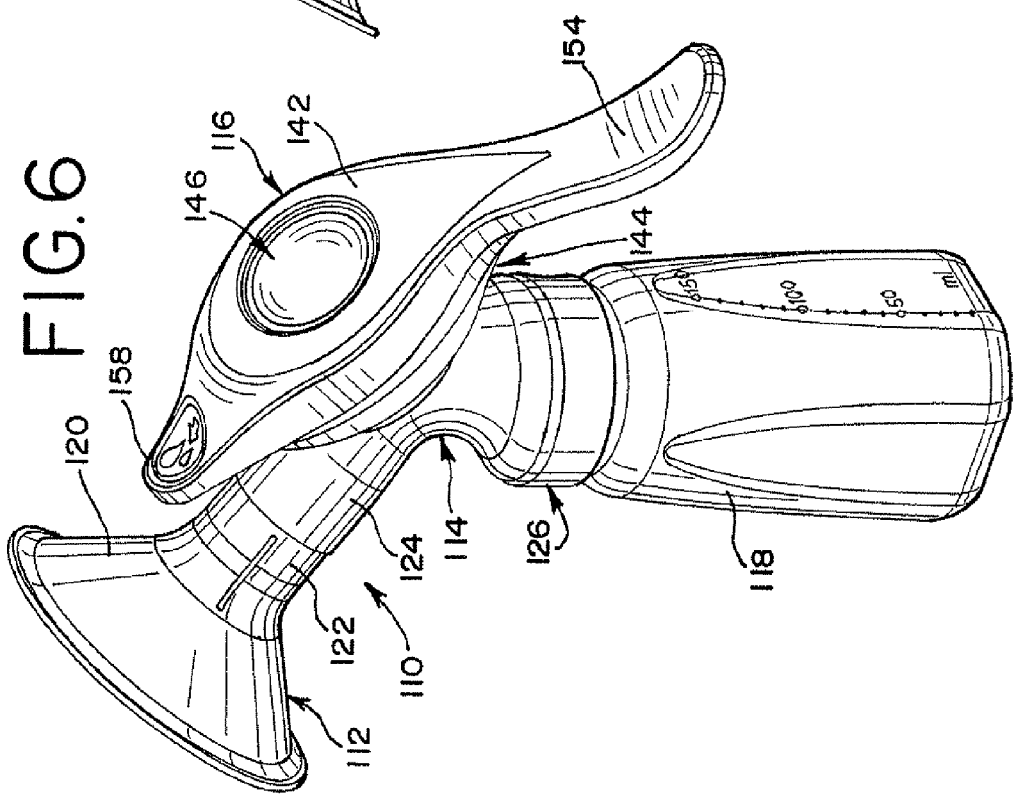

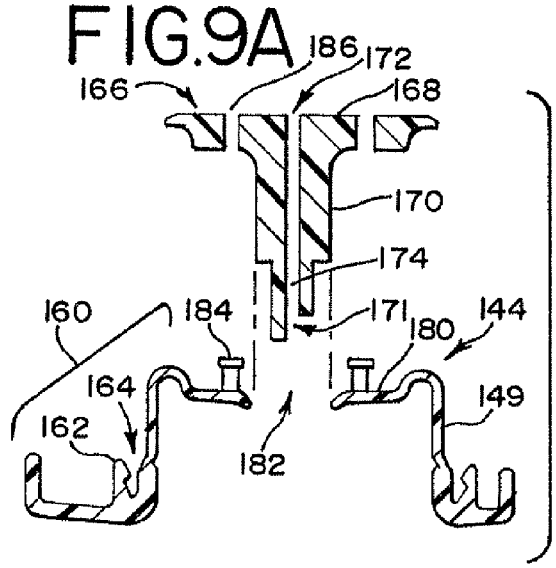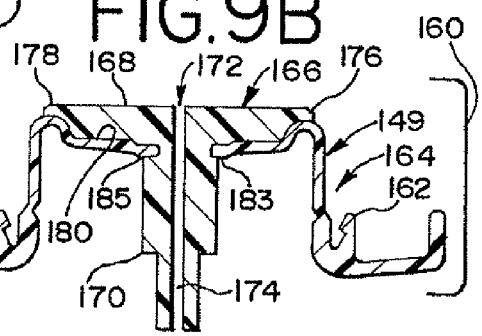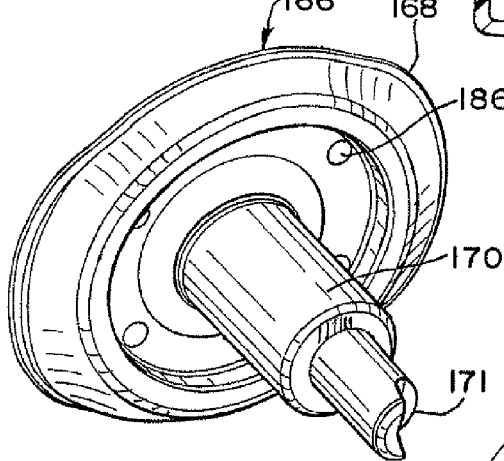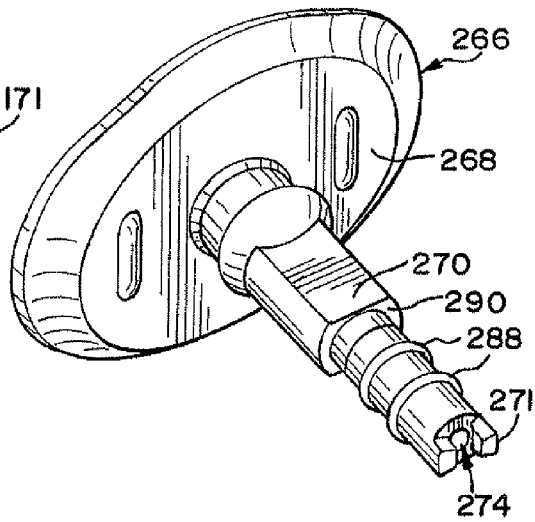

MANUAL BREASTPUMP WITH STIMULATION FEATURE

This application is a divisional of U.S. Ser. No. 10/424,887 filed Apr. 28, 2003, which in turn claims the benefit of U.S. Provisional Application No. 60/405,559, filed Aug. 23, 2002.

TECHNICAL FIELD

The present invention relates to a breastpump having a manually operated pump that is capable of one-handed operation. One aspect of the invention further includes a feature to stimulate a milk ejection reflex.

BACKGROUND OF THE INVENTION

Breastpumps for the purpose of extracting breastmilk from a nursing mother are well-known and generally comprise: a breastshield (also known as a shield) that is typically funnel-shaped and fits over the breast; a vacuum source connected to the breastshield for generating an intermittent vacuum within the breastshield such that milk is expressed from the breast; and a conduit structure for communicating milk from the breastshield to a receptacle for the expressed milk, as well as for communicating pressure variations (such as the foregoing vacuum) to the breastshield. While breastpumps that can be attached to motorized vacuum sources are available, there are occasions when mothers cannot conveniently plug a breastpump into an external vacuum source or an electrical outlet is not available. Battery-powered breastpumps are a good alternative. However a mother who wishes to draw milk from her breast (that is "express" milk) must, or otherwise may choose to, rely on a manual pump as the vacuum source.

Many manual pumps must be operated by two hands, one to hold the assembly in place and the other to drive the pump. One can refer, for example, to U.S. Pat. Nos. 4,857,051 and 6,110,140. Alternatively, manual pumps that do provide for one-handed use are often difficult to operate.

Moreover, existing manual breastpumps are not made to differentiate between different phases of the milk expression process, or equipped with a mechanism or method of operation to accommodate the different phases. That process includes, for example, a period before breastfeeding, referred to as the milk ejection period, or "letdown", in which effective removal of the milk from the breast is initiated by the suckling action of a baby's mouth and jaw to produce or stimulate an ejection reflex, in which stored milk is released and made available for expression.

The milk ejection reflex is the neurohormonal reflex resulting from the tactile stimulation of the nipple sending neuronal impulses to the hypothalamus, and the neurohypophysial release of oxytocin into the systemic circulation. The subsequent contraction of the myoepithelial cells within the breast caused by oxytocin moves milk from the alveoli into the collecting ducts and forward to the nipple. Milk ejection, or the milk ejection period, is the interval when an increased availability of milk from the nipple is caused as a result of the stimulation of the milk ejection reflex. Milk ejection in women normally lasts for approximately two minutes. The ejection reflex will be identified in the following also as "ejection".

The level of pressure applied and the intermittency of the stimulation for initiating ejection are different than the level and intermittency of the action for actually expressing the breast milk. Conventional manual breastpumps do not provide a method or mechanism by which a user can easily stimulate an ejection reflex and subsequently commence to efficiently express breastmilk.

A demand therefore is present for a breastpump that is used to easily produce stimulation to initiate ejection and in addition there is also demand for an improved breastpump that provides efficient expression of breastmilk by manual operation thereof. The present invention satisfies these demands, and others.

SUMMARY OF THE INVENTION

One broad aspect of the present invention provides a manual breastpump with a pump mechanism that operates in a mode to promote ejection. Another broad aspect of the invention is a truly novel pumping mechanism for one-handed operation of a manual breastpump. In one embodiment of the invention, a pump mechanism includes a single set of elements that may be operated so as to produce both ejection and general pumping. In another embodiment of the invention, the pump mechanism may include generally two sets of elements, each of which is designed so as to produce one of the modes of operation.

An object of one embodiment of the invention is to provide a handle of the breastpump with the operative mechanism built therein to produce a negative pressure or vacuum for conveyance to the shield of the assembly and application to a woman's breast. One more particular application of the object is an expansible chamber, e.g., a dome-like pocket, which is formed in the handle and is compressed and expanded by movement of the handle. For purposes of the present invention, the term handle contemplates any structure associated with the manual breast pump that is adapted to be manipulated by one or more hand of a user in operation of the pump mechanism.

One aspect of the present invention provides a manual breastpump assembly that includes a shield having an interior receiving surface, sized and shaped to receive a woman's nipple and at least some adjacent breast. A conduit structure extends to the shield. The conduit structure is in communication with the interior of the shield, whereas the conduit conveys air pressure changes to the interior of the shield and also conveys milk expressed from the breast. A pump mechanism is connected to the conduit structure. In a preferred form, the connection of the pump mechanism is releasable. The pump mechanism includes a handle portion and an expansible portion connected to the handle defining a vacuum chamber. The vacuum chamber is in communication with the shield, as by the conduit structure. The pump mechanism operably changes a volume of the vacuum chamber when manipulated by a user. The pump mechanism may be operative in a first mode of operation for producing a first change in the volume and a second mode of operation for producing a second change in the volume. In one embodiment of the invention, the first change is greater than the second change. This yields two different pressures at the breast. One of these pressures can be adapted as the novel letdown feature. In a particularly, preferred form of this aspect of the invention, movement of one part of the handle, such as a distal end (relative to the shield) produces one pressure. Movement of the other part of the handle, such as the proximal end, produces the other pressure. In another embodiment, the first and second change in volume is not different.

Another aspect of the invention provides a manual breastpump including a shield having an interior shield surface defining an interior. A base is provided to which the shield is mounted. A conduit structure is formed within the base including a conduit surface defining a conduit to channel milk expressed into the shield. A pressure chamber is defined at least in part by an interior sidewall structure of the base. The pressure chamber defines a chamber volume and has a chamber axis. A movable member is sealably mounted to the interior sidewall structure and is movable to change the chamber volume to produce a pressure change. An outlet is formed in the conduit structure through which the pressure change is communicated. The outlet communicates with the shield interior. A lever is directly connected to the movable member and is adapted for manipulation by a user's hand. The lever is operative in a first mode of operation and a second mode of operation. A pivot point is provided for the lever and is located radially from the chamber axis. The lever, when moved relative to the pivot point, causes the movable member to produce a change in volume by alternately increasing and decreasing the volume. The change in volume is relatively less when the lever is operated in the second mode of operation compared to the first mode of operation.

Another aspect of the invention provides an improved manual breastpump having an expression mechanism generating a primary vacuum for applying an intermittent pulling force upon a portion of a woman's breast placed within a shield for general pumping, wherein the improvement includes a manually operated ejection mechanism generating a secondary vacuum that is communicated to the shield. The secondary vacuum is of lesser absolute value in terms of pressure change communicated to the shield than the primary vacuum. The secondary vacuum ejection mechanism is preferably designed to enable rapid or staccato-like manipulative pressure pulses on the nipple/breast.

Another aspect of the invention provides a manual breastpump assembly including a shield with an interior receiving surface defining a shield interior within which at least a portion of a woman's breast is received. The shield is mounted to a shield base. A conduit structure is formed in the shield base with a conduit surface defining a conduit to channel milk expressed into the shield. An expression mechanism is attached to the conduit structure for generating a primary change in pressure at a first frequency. A port is formed in the shield base for conveying the primary change in pressure to be applied to the shield interior for the expression of milk and a manually operated ejection mechanism generates a secondary change in pressure at a second frequency, which is communicated to the shield and applied to at least part of the portion of the woman's breast therein. The secondary change in pressure may be of lesser absolute value communicated to the shield than the first change in pressure. The second frequency is higher than the first frequency for rapid pulses on the nipple/breast.

Another aspect of the invention provides a manually operated breastpump including a shield having an interior receiving surface that defines an interior that is sized and shaped to receive at least a portion of a woman's breast. The shield is mounted to a shield base. A conduit structure is formed within the shield base with a conduit surface defining a conduit to channel milk expressed into the shield. A pressure chamber is defined at least in part by an interior sidewall structure of the shield base. The pressure chamber defines a chamber volume and has a chamber axis. A movable member is sealably mounted to the pressure chamber and is movable to change the chamber volume within the pressure chamber to produce a change of pressure therein. An outlet is formed through the interior sidewall structure through which the change in pressure is communicated. A lever is directly connected to the movable member, and is adapted for manipulation by a user's hand. A pivot point for the lever is located radially from the chamber axis. The lever when moved relative to the pivot point causes the movable member to alternately increase and decrease the chamber volume. A manually operated ejection mechanism generates a secondary pressure change that is communicated to the shield and applied to at least part of the portion of the woman's breast therein. The manually operated ejection mechanism includes a flexible dome, a dome base to which the flexible dome is sealably mounted, and an outlet formed through the dome base in communication with the shield, the flexible dome being pressable by hand toward the dome base to thereby generate the secondary pressure.

Another aspect of the invention provides a method of operating a manual breastpump for expressing milk from a mother's breast including providing a manually operated breastpump, applying the breastpump to the breast, operating the manual breastpump in an ejection mode of operation to stimulate an ejection reflex, producing an ejection reflex in the mother and operating the manual breastpump in an expression mode of operation to generally express milk from the breast.

The objectives, advantages and features of the invention will be further appreciated upon consideration of the following detailed description of embodiments taken in conjunction with the drawings.

BRIEF DESCRIPTION OF THE DRAWINGS

FIG. 1 is a side view of an embodiment of a breastpump according to certain aspects of the present invention;

FIG. 2 is an exploded view of the breastpump of FIG. 1;

FIG. 3 is an enlarged perspective view of the breastpump of FIG. 1;

FIG. 4 is a perspective view of another embodiment of a breastpump (without the shield) according to certain aspects of the present invention;

FIG. 5 is a sectional view of the main vacuum chamber of the embodiment of the breastpump illustrated in FIG. 4 showing the pump drive mechanism;

FIG. 6 is a perspective view of yet another embodiment of a breastpump according to the present invention;

FIG. 7 is a side view of the breastpump of FIG. 6;

FIGS. 9A, and 9B is a sectional view of the diaphragm and puller of the pump mechanism of the breastpump of FIG. 6 and an alternate embodiment thereof;

FIG. 10 is a perspective view of the assembled puller shown in FIG. 9; and

FIG. 11 is a perspective view of another embodiment of a puller according to the present invention.

DETAILED DESCRIPTION OF EMBODIMENTS OF THE INVENTION

Figure 8:
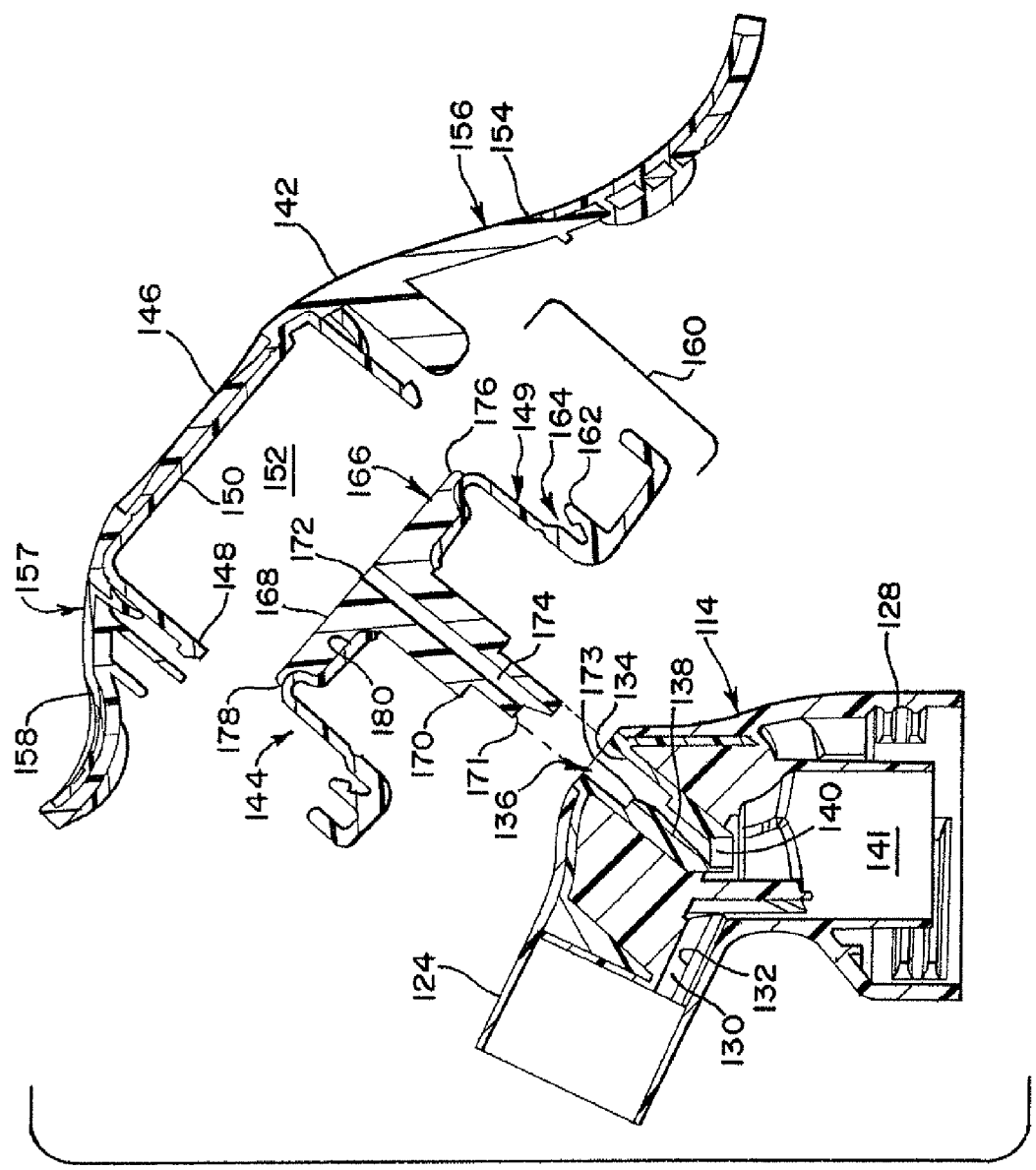
FIG. 8 is an expanded sectional view of the pump mechanism and conduit structure of the breastpump of FIG. 6.

FIG. 1 illustrates in broad overview an embodiment of a breastpump assembly 10 incorporating features of the present invention. The breastpump assembly includes a hood or shield 12, which extends into a tunnel or sleeve 14. Hood and shield are used interchangeably herein. A pressure-varying chamber in the form of a vacuum chamber 16 described in greater detail below is involved in the generation of changes in pressure for communication to the interior of the shield 12. A collar 18 may be provided for the releasable attachment of a milk bottle or like container (not shown) thereto. A conduit structure 19 connects and permits fluid communication between components of the breastpump assembly 10. For the purposes of this disclosure, the term "vacuum" connotes pressure reduction (e.g., below ambient pressure), sometimes also referred to herein as a negative pressure. While a vacuum is the desired negative pressure change being developed within the shield 12 from vacuum chamber 16, it need not be the only pressure change capable of being generated. A positive pressure (or overpressure) could be applied to squeeze the breast, for instance (the breast, of course, constituting at least the nipple, but typically also some surrounding breast tissue). Details of a breastpump having these general components, but not having the inventive features that are described herein, can be further gleaned from U.S. Pat. No. 6,110,140, for example.

As will be explained more fully below, the breastpump assembly 10 includes a pump mechanism (for example, see number 36 in FIG. 2) that is manually operable in a first mode of operation for the efficient expression of milk from a mother's breast (general pumping) and in a second mode of operation for stimulating an ejection reflex (letdown). As will be shown more fully herein, the breastpump assembly 10 pump mechanism 36, may be a single mechanism having two different operating modes; a milk expression mode of operation or an ejection mode of operation. In the alternate, the pump mechanism 36 may be two separate mechanisms; each separate mechanism designed to provide either a milk expression or an ejection mode of operation.

Further to the FIG. 1 embodiment, shield 12 and sleeve 14 attach to a shield mount 20, for example, in an interference fit. Shield 12 and sleeve 14 may be formed as a single unit or may be separate attachable units. The shield mount 20, conduit structure 19 and container collar 18 form base 21. For purposes of the present invention, the shape of the shield 12 and its formation with the base 21 of the breastpump assembly 10 are incidental; the particular arrangement and details of these elements is in no way limiting.

One embodiment of the present invention includes a conduit structure 19, having a conduit surface 23 that defines one or more internal conduits 25. Such a conduit structure 19 is shown in FIG. 5. The conduit structure 19 supports, connects and permits fluid communication between different termini such as between shield 12 at one terminus 11A, vacuum chamber 16 at a second terminus 11B, and a container (not shown) connected to collar 18 forming the third terminus 11C. As noted above, valve mechanism 24, such as the one described in U.S. Pat. No. 4,929,229, is releasably attached to the conduit structure 19. The valve mechanism 24, shown in FIGS. 1 and 2 includes a flexible disk 26, which provides a flap valve for opening and closing the valve mechanism 24 provides communication between conduit structure 19 and an attached bottle. When vacuum is provided in the three-way conduit structure 19 just described, the vacuum pulls flexible disk 26 against its seat, thereby sealing the conduit structure at this terminus. When the vacuum is released, breast milk in the conduit structure 19 may flow freely though valve mechanism 24 (past disk 26) into the bottle.

With reference to FIGS. 2, 3 and 5, one embodiment of the vacuum chamber 16 is defined, in part, by rigid continuous sidewall 28 with top wall 30. Sidewall aperture 38, formed through rigid outer sidewall 28 allows communication between vacuum chamber 16 and conduit 25. The pump mechanism 36 includes an upper rigid disc or plate 40, flexible membrane 42, diaphragm collar 44 and lever 46, such that the pump mechanism 36 is lever driven. The upper plate 40 is spaced from top wall 30, and with sidewall 28 define chamber 16. Lever 46 is rigidly connected to plate 40.

The pump mechanism 36 may include a collar 44 surrounding the circumference of the membrane 42, and a U-shaped channel 45 defined between spaced-apart sidewall portions 54, 56 sized and shaped to provide collar 44. The bottom edge 29 of the sidewall 28 is sized and shaped to fit snugly within the U-shaped channel 45 to mount the pump mechanism 36 within the vacuum chamber 16.

When inserted within the vacuum chamber 16, pump mechanism 36 is thereby generally sealed within vacuum chamber 16. When lever 46 is pulled towards the conduit structure 19, plate 40 pivots away from top wall 30 about a pivot point 31. A hinge-like action occurs between the flexible diaphragm collar 44 and the sidewall 28 at this point 31. A simple finger movement can move lever 46, as by a mother grasping the breastpump assembly 10 (in place on the breast) with one hand, and pulling the lever 46 towards the conduit structure 19, i.e., toward her body (and against the base as a stop). This causes the membrane 42 to collapse opposite the point 31. As the collapse of the membrane 42 causes the pump mechanism 36 to increase the volume of the chamber 16 (defined by walls 28 and 30, plate 40 and membrane 42) such that a vacuum is thereby created in the chamber 16 on the stroke towards the mother's body. The vacuum extends through aperture 38 into the conduit 25, reducing the pressure within and thereby applying or creating a condition of vacuum in the shield 12 and drawing air into chamber 16. When lever 46 is released, the natural resiliency of the membrane 42 causes the pump mechanism 36 to return to its rest position and occupy the chamber 16. Given that air may have been drawn into chamber 16, the return of the pump mechanism 36 to its rest position may cause a brief pressure condition above that of atmospheric pressure. The positive pressure thereby created can be used to open the flap valve 26 to assist in passing milk through the conduit 19 to the bottle or other container, with venting of the over-pressure through conventional means. A very easily operated one-handed manual pump mechanism 36 is thereby provided for operation in a first mode of operation for the efficient expression of breastmilk.

While a flexible membrane 42 has been described for the foregoing embodiment, other means to affect an expansible chamber-type device could also be employed for operation by a suitable lever. A movable or flexible member or a bellows-like arrangement could be used, or a hinged flap that sealingly engages against the interior sidewall structure for movement therein, just to name two variations.

One embodiment of the inventive breastpump also includes an ejection mechanism 32 for a second mode of operation of the breastpump assembly 10. As shown in FIG. 5, ejection mechanism 32 has a flexible dome-shaped ejection "button" 33 attached to top wall 30. Top wall 30 has an aperture 34 formed therethrough such that an ejection chamber 35 under ejection button 33 is permitted fluid communication with vacuum chamber 16. When ejection button 33 is depressed, as by a mother's finger, an initial positive pressure is created within the ejection chamber 35 and is communicated to vacuum chamber 16 by aperture 34. The initial positive pressure is in turn communicated to the conduit 25 from vacuum chamber 16 via sidewall aperture 38. When ejection button 33 is released, it returns under its own resiliency to an initial dome shape, and provides a slight vacuum within ejection chamber 35, which is, in turn transmitted through aperture 34 to vacuum chamber 16 in like manner. By pressing the button 33 in a rapid manner (relative to the operation of the general pump mechanism 36) a sequence is initiated, which can be referred to as an ejection sequence or a stimulation of the ejection reflex, which can be reminiscent of the initial suckling of an infant causing the onset of milk ejection, e.g., relatively rapid but light pulling and pushing upon the nipple and breast. Once ejection occurs, the mother uses pump mechanism 36 to create the main or primary intermittent vacuum sequence for milk expression.

It will be appreciated that the ejection mechanism 32 need not be an integral part of the breastpump assembly 10. The mechanism 32 could communicate with the breastpump assembly 10 via tubing (not shown), which may be attachable to the breastpump assembly 10 for instance to the conduit structure 19, and be operated by the hand that is not holding the breastpump assembly 10 in place on the breast. It is also not limited to a flexible dome in a push-button arrangement, as described in this embodiment, although a simple finger-operated mechanism like this is considered most desirable. The expansible chamber devices could be used.

The present invention may include a spring, elastomer or similar return device (not shown) by which the ejection button 33 may be urged back to a rest position from its pressed position. In such an embodiment, a spring could be disposed within chamber 35 between the top wall 30 and the button 33. The same or similar kind of assistant device could likewise be used with the primary pump mechanism 36 to place the lever 46 back to its initial or rest position.

FIG. 4 illustrates another embodiment of the present invention. The FIG. 4 embodiment includes lever 46' sized and shaped to accommodate the finger or fingers (not shown) of a user so as to provide an ergodynamic lever, having a smoothly curved outboard side 50. The lever 46' extends into a fastener 51, which connects with the plate 40.

In a preferred form, the outer surface 50 of the lever 46', as well as portions of the base (indicated at 60), is covered with a soft material for better grip and less stress on the hands. Thermoset elastomer or thermoplastic rubbers are just two generic types of material suitable for use as this soft outer layer.

Another embodiment of the present invention is illustrated in FIGS. 6-10. The breastpump assembly 110 includes a shield 112, for contacting the breast. The shield 112 is attached to a conduit structure 114. A vacuum pump mechanism 116 is attached to the conduit structure 114. The conduit structure 114 transmits vacuum generated in the vacuum pump mechanism 116 to the shield 112 and transmits expressed breastmilk from the shield to an attached container 118.

The shield 112 has a generally funnel shaped portion 120 shaped and sized for being received onto a breast. The shield 112 extends into a sleeve 122 downstream from the funnel shaped portion 120. The sleeve 122 is open so as to conduct expressed milk into the conduit structure 114. For purposes of the instant invention, the shape of the shield 112 and its formation with the conduit structure 114 are incidental; the particular arrangement and details of these elements is in no way limiting.

The conduit structure 114 is attachable to the shield 112 through a shield mount 124 sized and shaped to receive the sleeve 122. The conduit structure 114 is generally a housing that interconnects and permits fluid communication between parts of the breastpump assembly 110. The conduit structure 114 connects to the sleeve 122, by way of the shield mount 124 at the one end, and terminates with a valve mechanism (see FIG. 2, for example) as is known in the art at a container end 126. The container end 126 may include threads 128 or any suitable mechanism for releasable attachment to container 118, which may be in the form of a milk bottle or the like.

The conduit structure 114 includes a first conduit 130 defined by an inner first conduit surface 132 for conducting expressed breast milk from the shield mount 124 through the valve mechanism and into the container 118. The conduit structure 114 includes a receptacle 134 for receiving the pump mechanism 116. The receptacle 134 may be a bore formed in the conduit structure 114 or a bore formed in a cylindrical extension (not shown) of the conduit structure 114. The receptacle 134 further includes a longitudinal bore 138 in fluid communication with a second conduit 140 for transmitting pressure changes generated in the pump mechanism 116 through the receptacle 134 and conduit structure 114. The second conduit 140 is in fluid communication with the first conduit 130 in chamber 141 so as to conduct pressure changes through the conduit structure 114 to the shield 112 and thence to a breast of a user.

The pump mechanism 116 is releasably and even rotatably attachable to the conduit structure 114. The pump mechanism 116 includes two main portions. A first portion is a substantially rigid shell or handle 142. The second portion is a flexible movable member in the form of a diaphragm-like structure 144 attached to the handle. The handle 142 may be made of a rigid plastic similar to that of the conduit structure 114. Referring to FIG. 8 in particular, handle 142 has a central portion 146, which has the form of a dome or housing, and a bottom edge portion 148. The dome 146 includes an inner surface 150, which defines a vacuum chamber 152 with the diaphragm 144 as will be explained more fully below.

The handle 142 includes a first extension 154 in the form of a handle extending from a back side 156 of the handle 142, which is sized and shaped to be grasped by a hand or one or more digits of the user. Drawing the distal or first extension 154 toward the conduit structure 114 and generally toward the user's body operates the first extension 154 in the first mode of operation of the breastpump. A second or proximal extension 158 extends from the front side 157, opposite the first extension 154, in the form of a tab or smaller handle extension. The proximal or second extension 158 may be smaller than the first 154 and may be operated by drawing the extension downwardly toward the conduit structure 114 in the second mode of operation with a single digit of the user. Distal and proximal are used herein relative to the shield 112.

The diaphragm 144 includes two main parts. A first part is a flexible portion 160, shaped like an inverted cup to be positioned inside the dome 146 of the handle 142 adjacent the inner surface 150 thereof. The flexible portion 160 includes an outer edge 162 with a channel 164 for tightly fitting with the dome shell edge 148. The flexible portion 160 is made of a naturally resilient material so that there is a tendency for the membrane to be resiliently returned to a starting position after being deflected in use. The membrane 160 includes a central concavity 180 on an upper surface thereof and a central opening 182 (FIG. 9) to receive a puller 166. There is a thinned transition area 149 defining the middle of the flexible portion 160.

The second part of the diaphragm 144 is a rigid member or puller 166. The puller 166 includes a disc portion 168 and an extension or post 170. The disc portion 168 is a generally flattened oval member that is centrally imbedded within or attached to the membrane 160 at the upper surface concavity 180 and may be held in place by posts 184 (FIG. 9) of the membrane 160 inserted through holes 186, for example, such as four holes 186 arranged somewhat symmetrically around the disc portion. The disc portion 168 includes a central opening 172 that is open to the vacuum chamber 152 at an upper end thereof. The post 170 is a hollow cylindrical member that is attached to the disc portion 168. A hollow bore 174 of the post 170 is aligned to be in communication with the central opening 172 of the disc portion 168. The extension 170 is sized and shaped to be received within the post receptacle 134, preferably via a press or interference fit. Preferably, the connection of the extension 170 to the post receptacle 134 is releasable and rotatable or pivotable in the receptacle 134. In this manner, the entire handle 116 and extension 154 may be rotated to one side of the breastpump assembly for the convenience of the user. In an alternate embodiment, the puller 166 may be fixedly connected to the conduit structure 114. In yet another embodiment, the assembly 110 may be formed as a unitary unit. For ease of cleaning, it is preferred to provide the various elements of the assembly 110 as separate elements. Accordingly, for the purpose of this invention, the term connected may refer to a releasable or a permanent connection.

In one preferred embodiment, the lower end of the post 170 forms a half-lap feature 171, which when fitted to the receptacle 134 cooperates with a converse feature 173 within the bore of socket 134 to limit the arcuate travel of handle 116 and prevent over-rotation. FIG. 9A shows another way of mounting a modified disc portion 168 and membrane 160. Here, the opening 182 in the membrane is further defined by a thickened ring or bead 183, which depends from a bottom surface opposite the concavity 180. Post 170 has a complementary channel 185 formed thereon, in which the bead 183 seats.

In operation, at a rest position, which is a start or initial position, the pump mechanism membrane 160 lies against or closely adjacent to the inner surface 150 of the dome portion 146 of the handle 142. In this position, as shown in FIG. 6, the volume of the vacuum chamber 152 is zero or at a minimum volume. When the user manipulates the first extension 154 by pulling the extension inwardly toward the conduit structure 114, the post 170 and disc portion 168 remain connected to and motionless with respect to the conduit structure while the handle 142 moves with the extension. The rigid disc portion 168 pivots about a point at a rear edge 176 thereof, causing the membrane 160 to pull away from the inner surface 150 of the dome 146, which expands the vacuum chamber 152 a first volume to produce a first negative pressure therein. The reduced pressure is communicated through the central opening 172 of the disc 168, through the hollow bore 174 of the post 170, through the longitudinal bore 138 of the receptacle 134, through the second conduit 140 and thence the shield 112. Operation of the breastpump 110 by this first mode of operation is intended to generate an amount of vacuum at a cyclical rate in order to efficiently promote milk expression from a breast, i.e., general pumping. A very easily operated one-handed manual pump mechanism is thereby provided that operates a manual breastpump in a first mode of operation to produce an efficient expression of breast milk, with a milk expression mechanism comprising first extension 154 and an associated edge pivot point 176. Note also that the handle 142 freely rotates in receptacle 134, enabling the user to adjust the handle's position to a most convenient grasping orientation.

When the user manipulates the second extension 158 by pulling that extension downwardly (e.g., toward the conduit structure 114) in a second mode of operation, the membrane 160 pulls away from the inner surface 150 of the dome 146 at a distal region by pivoting about a point at a front edge 178 of the disc, which expands the vacuum chamber 152 a second volume to produce a second negative pressure therein.

The second volume may be less than the first volume so that a lesser relative change in pressure is generated by the second mode of operation as compared to the first mode. In the present embodiment, this difference may be due to the shape and travel of the first and second extensions 154, 158. That is, second extension travels a shorter distance before it is stopped by the hood mount 124. First extension 154 has a longer distance of travel before it is stopped by the conduit structure 114. In an alternate embodiment (not shown), the depth of the vacuum chamber adjacent the second extension 158 may be formed as to be greater than the depth of the chamber adjacent the first extension 154. When the pull of the puller 166 causes the membrane 160 to pull away from the inner surface 150 of the dome 146, a relatively greater change in volume is created in operation of the first extension 154 due to the greater depth of the resultant chamber as compared to manipulation of the second extension 158.

Operation of the breastpump 110 by the second mode of operation is intended to generate an amount of vacuum (relatively less in absolute change) at a cyclical rate (which may be relatively more rapid) in order to efficiently promote a milk ejection reflex. It can be seen that use of a small extension 158 is possible and efficient to promote ejection due to the lesser amount of vacuum generated in the second mode of operation. Because of the lesser amount of force necessary the second mode of operation may occur relatively more rapidly, which, it has been found, is desired to produce ejection as compared to expression. The second mode of operation produces ejection with a milk ejection mechanism comprising extension 158 and an associated edge pivot point 178.

It will be appreciated that other means may be employed to provide the illustrated breastpump with first and second modes of operation according to that inventive concept herein, wherein the pump mechanism is capable of generating both ejection and expression operation. For example, limiting the travel of either the extension 154, 158 and displacement of the diaphragm thereby creates a relatively lesser change in pressure when compared to the first mode of operation. For example, the extension 154 may be permitted to travel a distance in the first mode of operation to produce a vacuum designed to efficiently express milk, e.g., from about 100-250 mmHg. The extension 154 or 158 may be permitted to travel a distance in the second mode of operation to produce a negative pressure change designed to stimulate an ejection reflex, e.g., from about 50-150 mmHg. The frequency of intermittent operation of the extension 158 during the ejection mode of operation may be twice the frequency or greater than that used during the expression mode of operation. Further, because the travel is limited in the second mode of operation, the frequency of movement of the extension 158 can be easily increased as compared to the operation of the pump mechanism 116 in the first mode of operation. The second mode of operation, including operating the breastpump 110 at a relatively higher frequency and a relatively lower change in pressure produces letdown in the nursing mother much more successfully than operation of the breastpump in a set of conditions designed for general expression of milk.

In another embodiment of the present invention, indicia (not shown) could be provided to assist the user in determining the amount of travel or displacement of the pump mechanism 116 in order to vary the pumping conditions and parameters to provide the first and second modes of operation with a single extension. Further, stops could be adopted for regulating the travel of the extension 154 correspondingly to "Max", "Med" and "Min" levels of vacuum.

FIG. 11 shows another embodiment of a puller 266 for use in the breastpump of the present invention. The depicted puller generally has the same function of the puller shown in FIGS. 8-10. The puller 266 includes a disc portion 268 connected or integrally molded with a extension 270. The disc portion 268 may be oval as depicted or any suitable shape. The extension 270 may be essentially cylindrical post with a hollow axial bore 274. The distal end of the extension 270 includes a stop feature 271 which permits rotation of the puller a predetermined amount. In this manner, the handle (see FIG. 6) pivots and the breastpump are usable in a great array of configurations. This embodiment of the puller 266 includes o-rings 288 fitted about a mid-span of the extension 270. It will be understood that the o-rings 288 provide a fluid-tight seal with a corresponding socket (see FIG. 8) of the breastpump and permits rotation of the handle with respect to the conduit to which it is attached. Furthermore, the extension 270 includes a shoulder 290, which limits the insertion of the extension.

While particular embodiments of the present invention are disclosed herein, it will be understood that such embodiments are examples of an invention that may encompass various and alternative forms. Therefore, the specific structural and functional details disclosed herein are not intended to be limiting, but merely exemplify the literal and equivalent scope of the invention as claimed below.

What is claimed is:

1. An improved manual breastpump having a milk expression mechanism generating a primary pressure for applying an intermittent force upon a portion of a woman's breast placed within a shield, wherein the improvement comprises:
   a manually operated ejection mechanism means for generating a secondary pressure which is less than said primary pressure that is communicated to said shield to cause letdown.

2. The breastpump of claim 1 wherein the shield is connected to a shield base having a conduit structure, said conduit structure conveying said pressures to the shield and through which milk expressed from the breast is carried from the shield to a container.

3. The breastpump of claim 2 wherein said manually operated ejection mechanism means is sized and located to be operated by a finger of the mother, said shield base being adapted to be grasped in one hand.

4. The breastpump of claim 1 wherein said ejection mechanism means is operable in a generally rapid manner relative to a frequency of said primary pressure generated in the operation of said expression mechanism.

5. A manual breastpump comprising:
   a shield having an interior receiving surface which defines an interior which is sized and shaped to receive at least a portion of a woman's breast;
   a conduit structure;
   a milk expression mechanism including a primary manual pump for providing a primary intermittent change of pressure to be applied to said shield interior for the expression of milk; and
   a manually operated milk ejection mechanism means for generating a secondary intermittent pressure change for the stimulation of a milk letdown reflex, said secondary intermittent pressure change being communicated to said shield interior and applied to at least part of said portion of the woman's breast therein.

6. The manual breastpump of claim 5 wherein said secondary intermittent pressure change is of a lesser absolute value in terms of pressure change communicated to said shield than said primary intermittent pressure change, said manually operated ejection mechanism being operable in a generally rapid manner relative to said primary manual pump.

7. The manual breastpump of claim 5 wherein said manually operated ejection mechanism means comprises:
   a flexible dome;
   a dome base to which said flexible dome is sealably mounted; and
   an outlet formed through said dome base in communication with said shield, said flexible dome being pressable by hand toward said dome base to thereby generate said secondary intermittent pressure.

8. The manual breastpump of claim 5 wherein said primary manual pump mechanism comprises:
   a diaphragm sealably mounted to said conduit structure and defining with said conduit structure a pressure chamber; and
   a lever directly connected to said diaphragm, said lever being pivotable about a pivot point to thereby generate said primary pressure change.

9. An improved breastpump having a milk expression mechanism generating a primary pressure for applying an intermittent force upon a portion of a woman's breast placed within a shield, wherein the improvement comprises:
   a manually operated ejection mechanism means for stimulating a letdown reflex of the woman.

* * * * *